US010054583B2

(12) United States Patent
Perez-Leal et al.

(10) Patent No.: US 10,054,583 B2
(45) Date of Patent: Aug. 21, 2018

(54) NUCLEAR FACTOR-ERYTHROID 2 RELATED FACTOR 2 (NRF2) BIOSENSORS AND MODULATORS OF NRF2

(71) Applicant: TEMPLE UNIVERSITY OF THE COMMONWEALTH SYSTEM OF HIGHER EDUCATION, Philadelphia, PA (US)

(72) Inventors: Oscar M. Perez-Leal, Philadelphia, PA (US); Salim Merali, Bryn Mawr, PA (US); Carlos A. Barrero, Philadelphia, PA (US)

(73) Assignee: TEMPLE UNIVERSITY OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 14/435,000

(22) PCT Filed: Oct. 9, 2013

(86) PCT No.: PCT/US2013/064069
§ 371 (c)(1),
(2) Date: Apr. 10, 2015

(87) PCT Pub. No.: WO2014/058982
PCT Pub. Date: Apr. 17, 2014

(65) Prior Publication Data

US 2016/0146785 A1 May 26, 2016

Related U.S. Application Data

(60) Provisional application No. 61/830,942, filed on Jun. 4, 2013, provisional application No. 61/711,984, filed on Oct. 10, 2012.

(51) Int. Cl.

| | |
|---|---|
| ***G01N 33/50*** | (2006.01) |
| ***C12Q 1/68*** | (2018.01) |
| ***C12Q 1/6883*** | (2018.01) |
| ***A61K 31/05*** | (2006.01) |
| ***A61K 31/136*** | (2006.01) |
| ***A61K 31/225*** | (2006.01) |
| ***A61K 31/353*** | (2006.01) |
| ***C07K 14/47*** | (2006.01) |
| ***C12Q 1/6897*** | (2018.01) |

(52) U.S. Cl.

CPC ......... *G01N 33/5023* (2013.01); *A61K 31/05* (2013.01); *A61K 31/136* (2013.01); *A61K 31/225* (2013.01); *A61K 31/353* (2013.01); *C07K 14/4701* (2013.01); *C12Q 1/6883* (2013.01); *C12Q 1/6897* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 2002/0049176 | A1* | 4/2002 | Anderson | C07K 14/4705 514/44 R |
| 2002/0164576 | A1 | 7/2002 | Pedersen et al. | |
| 2007/0224635 | A1* | 9/2007 | Bouquin | G01N 33/502 435/7.1 |
| 2009/0176260 | A1* | 7/2009 | Wu | C12N 5/0603 435/8 |
| 2011/0112196 | A1* | 5/2011 | Lukashev | G01N 33/502 514/574 |
| 2011/0136246 | A1* | 6/2011 | Shibata | C12Q 1/6886 436/94 |
| 2011/0206615 | A1 | 8/2011 | Miyawaki et al. | |

OTHER PUBLICATIONS

NM_006164.3 (*Homo sapiens* nuclear factor (erythroid-derived 2—like 2 (NFE2L2), transcript variant 1, mRNA, NCBI Reference Sequence, priority to Oct. 9, 2011, 5 pages).*
Nioi et al. (2005) The Carboxy-Terminal Neh3 Domain of Nrf2 Is Required for Transcriptional Activation. Molecular and Cellular Biology, 25(24):10895-10906.*
Baur et al. (2006) Therapeutic potential of resveratrol: the in vivo evidence. Nature Reviews Drug Discovery, 5:496-506.*
Nioi, Paul et al., "The Carboxy-Terminal Neh3 Domain of Nrf2 is Required for Transcriptional Activation," Molecular and Cellular Biology, Dec. 2005, vol. 25, No. 24, p. 10895-10906.
International Search Report and Written Opinion dated Apr. 28, 2014 for corresponding PCT Application No. PCT/US13/64069.
NCBI Reference Sequence: NM_006164.4 '*Homo sapiens* nuclear factor (erythroid-derived 2)-like 2 (NFE2L2), transcript variant 1, mRNA', retrieved on Apr. 1, 2014 from http://www.ncbi.nlm.nih.gov/nuccore/NM_006164.

* cited by examiner

*Primary Examiner* — Neil P Hammell
(74) *Attorney, Agent, or Firm* — Duane Morris LLP

(57) ABSTRACT

Compositions include nucleic acid sequences encoding the C-terminal fragment of fragment (Seg3) of Nuclear factor-erythroid 2 related factor 2 (Nrf2). These compositions provide a target for identification of novel therapeutics having the ability to modulate the translation of Nrf2. Methods of treating subjects are also provided.

6 Claims, 7 Drawing Sheets

Apigenin

Resveratrol

Amino resveratrol sulfate

Triacetylresveratrol

Apigenin

Quercetin

Luteolin

SEQUENCE LISTING

```
<160> NUMBER OF SEQ ID NOS: 5

<210> SEQ ID NO 1
<211> LENGTH: 1818
<212> TYPE: DNA
<213> ORGANISM: Homo sapiens

<400> SEQUENCE: 1

atgatggact tggagctgcc gccgccggga ctcccgtccc agcaggacat ggatttgatt      60

gacatacttt ggaggcaaga tatagatctt ggagtaagtc gagaagtatt tgacttcagt     120

cagcgacgga aagagtatga gctggaaaaa cagaaaaaac ttgaaaagga aagacaagaa     180

caactccaaa aggagcaaga gaaagccttt ttcgctcagt tacaactaga tgaagagaca     240

ggtgaatttc tcccaattca gccagcccag cacatccagt cagaaaccag tggatctgcc     300

aactactccc aggttgccca cattcccaaa tcagatgctt tgtactttga tgactgcatg     360

cagcttttgg cgcagacatt cccgtttgta gatgacaatg aggtttcttc ggctacgttt     420

cagtcacttg ttcctgatat tcccggtcac atcgagagcc cagtcttcat tgctactaat     480

caggctcagt cacctgaaac ttctgttgct caggtagccc ctgttgattt agacggtatg     540

caacaggaca ttgagcaagt ttgggaggag ctattatcca ttcctgagtt acagtgtctt     600

aatattgaaa atgacaagct ggttgagact accatggttc caagtccaga agccaaactg     660

acagaagttg acaattatca tttttactca tctataccct caatggaaaa agaagtaggt     720

aactgtagtc cacattttct taatgctttt gaggattcct tcagcagcat cctctccaca     780

gaagacccca accagttgac agtgaactca ttaaattcag atgccacagt caacacagat     840

tttggtgatg aattttattc tgctttcata gctgagccca gtatcagcaa cagcatgccc     900

tcacctgcta ctttaagcca ttcactctct gaacttctaa atgggcccat tgatgtttct     960

gatctatcac tttgcaaagc tttcaaccaa aaccaccctg aaagcacagc agaattcaat    1020

gattctgact ccggcatttc actaaacaca agtcccagtg tggcatcacc agaacactca    1080

gtggaatctt ccagctatgg agacacacta cttggcctca gtgattctga agtggaagag    1140

ctagatagtg cccctggaag tgtcaaacag aatggtccta aaacaccagt acattcttct    1200

ggggatatgg tacaaccctt gtcaccatct caggggcaga gcactcacgt gcatgatgcc    1260
```

-continued

```
caatgtgaga acacaccaga gaaagaattg cctgtaagtc ctggtcatcg gaaaacccca   1320

ttcacaaaag acaaacattc aagccgcttg gaggctcatc tcacaagaga tgaacttagg   1380

gcaaaagctc tccatatccc attccctgta gaaaaaatca ttaacctccc tgttgttgac   1440

ttcaacgaaa tgatgtccaa agagcagttc aatgaagctc aacttgcatt aattcgggat   1500

atacgtagga ggggtaagaa taaagtggct gctcagaatt gcagaaaaag aaaactggaa   1560

aatatagtag aactagagca agatttagat catttgaaag atgaaaaaga aaaattgctc   1620

aaagaaaaag gagaaaatga caaaagcctt cacctactga aaaaacaact cagcacctta   1680

tatctcgaag ttttcagcat gctacgtgat gaagatggaa aaccttattc tcctagtgaa   1740

tactccctgc agcaaacaag agatggcaat gttttccttg ttcccaaaag taagaagcca   1800

gatgttaaga aaaactag                                                 1818
```

<210> SEQ ID NO 2
<211> LENGTH: 660
<212> TYPE: DNA
<213> ORGANISM: Homo sapiens

<400> SEQUENCE: 2

```
agtgtcaaac agaatggtcc taaaacacca gtacattctt ctggggatat ggtacaaccc     60

ttgtcaccat ctcaggggca gagcactcac gtgcatgatg cccaatgtga gaacacacca    120

gagaaagaat tgcctgtaag tcctggtcat cggaaaaccc cattcacaaa agacaaacat    180

tcaagccgct tggaggctca tctcacaaga gatgaactta gggcaaaagc tctccatatc    240

ccattccctg tagaaaaaat cattaacctc cctgttgttg acttcaacga aatgatgtcc    300

aaagagcagt tcaatgaagc tcaacttgca ttaattcggg atatacgtag gaggggtaag    360

aataaagtgg ctgctcagaa ttgcagaaaa agaaaactgg aaaatatagt agaactagag    420

caagatttag atcatttgaa agatgaaaaa gaaaaattgc tcaaagaaaa aggagaaaat    480

gacaaaagcc ttcacctact gaaaaaacaa ctcagcacct tatatctcga agttttcagc    540

atgctacgtg atgaagatgg aaaaccttat tctcctagtg aatactccct gcagcaaaca    600

agagatggca atgttttcct tgttcccaaa agtaagaagc cagatgttaa gaaaaactag    660
```

<210> SEQ ID NO 3
<211> LENGTH: 2313
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3

```
atggaagatg ccaaaaacat taagaagggc ccagcgccat tctacccact cgaagacggg     60

accgccggcg agcagctgca caaagccatg aagcgctacg ccctggtgcc cggcaccatc    120

gcctttaccg acgcacatat cgaggtggac attacctacg ccgagtactt cgagatgagc    180

gttcggctgg cagaagctat gaagcgctat gggctgaata caaaccatcg gatcgtggtg    240

tgcagcgaga atagcttgca gttcttcatg cccgtgttgg gtgccctgtt catcggtgtg    300

gctgtggccc cagctaacga catctacaac gagcgcgagc tgctgaacag catgggcatc    360

agccagccca ccgtcgtatt cgtgagcaag aaagggctgc aaaagatcct caacgtgcaa    420

aagaagctac cgatcataca aaagatcatc atcatggata gcaagaccga ctaccagggc    480

ttccaaagca tgtacacctt cgtgacttcc catttgccac ccggcttcaa cgagtacgac    540
```

-continued

```
ttcgtgcccg agagcttcga ccgggacaaa accatcgccc tgatcatgaa cagtagtggc    600

agtaccggat tgcccaaggg cgtagcccta ccgcaccgca ccgcttgtgt ccgattcagt    660

catgcccgcg accccatctt cggcaaccag atcatccccg acaccgctat cctcagcgtg    720

gtgccatttc accacggctt cggcatgttc accacgctgg gctacttgat ctgcggcttt    780

cgggtcgtgc tcatgtaccg cttcgaggag gagctattct tgcgcagctt gcaagactat    840

aagattcaat ctgccctgct ggtgcccaca ctatttagct tcttcgctaa gagcactctc    900

atcgacaagt acgacctaag caacttgcac gagatcgcca gcggcggggc gccgctcagc    960

aaggaggtag gtgaggccgt ggccaaacgc ttccacctac caggcatccg ccagggctac   1020

ggcctgacag aaacaaccag cgccattctg atcacccccg aaggggacga caagcctggc   1080

gcagtaggca aggtggtgcc cttcttcgag gctaaggtgg tggacttgga caccggtaag   1140

acactgggtg tgaaccagcg cggcgagctg tgcgtccgtg gccccatgat catgagcggc   1200

tacgttaaca accccgaggc tacaaacgct ctcatcgaca aggacggctg gctgcacagc   1260

ggcgacatcg cctactggga cgaggacgag cacttcttca tcgtggaccg gctgaagagc   1320

ctgatcaaat acaagggcta ccaggtagcc ccagccgaac tggagagcat cctgctgcaa   1380

caccccaaca tcttcgacgc cggggtcgcc ggcctgcccg acgacgatgc cggcgagctg   1440

cccgccgcag tcgtcgtgct ggaacacggt aaaaccatga ccgagaagga gatcgtggac   1500

tatgtggcca gccaggttac aaccgccaag aagctgcgcg gtggtgttgt gttcgtggac   1560

gaggtgccta aaggactgac cggcaagttg gacgcccgca agatccgcga gattctcatt   1620

aaggccaaga agggcggcaa gatcgccgtg taaagtgtca aacagaatgg tcctaaaaca   1680

ccagtacatt cttctgggga tatggtacaa cccttgtcac catctcaggg gcagagcact   1740

cacgtgcatg atgcccaatg tgagaacaca ccagagaaag aattgcctgt aagtcctggt   1800

catcggaaaa ccccattcac aaaagacaaa cattcaagcc gcttggaggc tcatctcaca   1860

agagatgaac ttagggcaaa agctctccat atcccattcc ctgtagaaaa aatcattaac   1920

ctccctgttg ttgacttcaa cgaaatgatg tccaaagagc agttcaatga agctcaactt   1980

gcattaattc gggatatacg taggaggggt aagaataaag tggctgctca gaattgcaga   2040

aaaagaaaac tggaaaatat agtagaacta gagcaagatt tagatcattt gaaagatgaa   2100

aaagaaaaat tgctcaaaga aaaaggagaa aatgacaaaa gccttcacct actgaaaaaa   2160

caactcagca ccttatatct cgaagttttc agcatgctac gtgatgaaga tggaaaacct   2220

tattctccta gtgaatactc cctgcagcaa acaagagatg gcaatgtttt ccttgttccc   2280

aaaagtaaga agccagatgt taagaaaaac tag                                2313
```

```
<210> SEQ ID NO 4
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

tcggttaagc aaaacggccc aaagacgccc gtccactcgt caggtgacat ggtccagcca     60

ctgtccccct cgcaaggaca aagtacgcat gtacacgacg ctcagtgcga aaataccccc    120

gaaaaggagc tacccgtgtc ccccgggcac agaaagacgc cctttacgaa ggataagcac    180

tcctccaggt tagaagccca cctaacgcgc gacgagctcc gagcgaaggc gttacacata    240
```

-continued

```
ccctttcccg tggagaagat aataaatttg ccggtagtcg attttaatga gatgatgagt    300

aaggaacaat ttaacgaggc ccagctagcg ttgataaggg acatcagacg ccgaggaaaa    360

aacaaggtag cagcgcaaaa ctgtcggaag cggaagttag agaacatcgt ggagctcgaa    420

caggacctcg accacctaaa ggacgagaag gagaagctcc taaaggagaa gggggagaac    480

gataagtcat tgcatttgct aaagaagcag ttgtcgactt tgtacttaga ggtattttct    540

atgttgcggg acgaggacgg caagccctac tcgccctcag agtattcgct ccaacagacc    600

cgagacggta acgtctttct agtccctaag tccaaaaaac ccgacgtgaa aaagaat       657


<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

His His His His His His
1               5
```

NUCLEAR FACTOR-ERYTHROID 2 RELATED FACTOR 2 (NRF2) BIOSENSORS AND MODULATORS OF NRF2

CROSS-REFERENCE TO RELATED APPLICATIONS

The present application is a U.S. national phase application filed under 35 U.S.C. § 371 of International Application No. PCT/US 2013/064069, which was filed Oct. 9, 2013 and which claims priority to U.S. provisional application Ser. No. 61/711,984 filed on Oct. 10, 2012 and U.S. provisional application Ser. No. 61/830,942 filed Jun. 4, 2013, which are incorporated herein by reference in their entirety.

SEQUENCE LISTING

The instant application contains a Sequence Listing which has been submitted electronically in ASCII format and is hereby incorporated by reference in its entirety. Sais ASCII copy, created on Nov. 5, 2013, is named F5129-00021_SL.txt and is 8,242 bytes in size.

FIELD OF THE INVENTION

Embodiments of the invention are directed to compositions of Nuclear factor-erythroid 2 related factor 2 (Nrf2). The compositions are used, in part, to identify novel therapeutics by measuring the translation of these Nrf2 compositions in the presence or absence of a particular compound. Direct modulators of Nrf2, independent of Nrf2-Keap1 interactions, are identified. Methods of treatment are also provided.

BACKGROUND

Numerous endogenous and exogenous oxidative and electrophilic chemicals such as reactive oxygen species (ROS) and nitrogen species (RNS) constantly assault the human body. Prolonged exposure to the ROS can cause oxidative damage to cells that eventually leads to chronic inflammation, a hallmark of many diseases and aging. To protect against harmful effects of the ROS, the cells use an extensive array of both endogenous (enzymes and metabolites) and exogenous (nutrients) antioxidants. Many studies have investigated the therapeutic potential of antioxidant vitamins or supplements such as vitamins C and E, carotenoids, N-acetylcysteine, and other compounds that react stoichiometrically with ROS. The results of studies involving supplemental direct antioxidants have been quite disappointing overall. This is likely because exogenous antioxidant compounds, which react stoichiometrically with oxidants, cannot be orally consumed or distributed throughout the body in large enough quantities to meet the oxidative stress demand. Additionally, redox balance in mammalian biology is maintained by endogenous enzyme systems as opposed to directly-reacted exogenous compounds.

SUMMARY

This Summary is provided to present a summary of the invention to briefly indicate the nature and substance of the invention. It is submitted with the understanding that it will not be used to interpret or limit the scope or meaning of the claims.

ROS are quenched in vivo by powerful and ubiquitous cellular pathways of antioxidant enzymes, and, without wishing to be bound by any theory, the best approach to improve antioxidant defenses is by inducing the network of antioxidant enzymes by acting on their regulatory pathways.

In some embodiments, a biosensor comprises an isolated nucleic acid or cDNA or cDNA sequence encoding a C-terminal fragment (Seg3) of Nuclear factor-erythroid 2 related factor 2 (Nrf2) operably linked to a detectable moiety. In preferred embodiments, the isolated nucleic acid or cDNA or cDNA comprises at least one stop codon between the C-terminal Nrf2 fragment and the detectable moiety. In other embodiments, the C-terminal Nrf2 fragment and the detectable moiety optionally comprise one or more linker molecules.

In some embodiments, the biosensor comprises at least about a 50% sequence identity to SEQ ID NO: 3. In other embodiments, the biosensor comprises at least about 75%, 80%, 85%, 90%, 95%, 96%, 97%, 98%, 99% sequence identity to SEQ ID NO: 3. In other embodiments, the biosensor sequence is set forth as SEQ ID NO: 3.

In another embodiment, an isolated nucleic acid or cDNA comprises a C-terminal fragment (Seg3) of Nuclear factor-erythroid 2 related factor 2 (Nrf2) operably linked to a detectable moiety and at least one stop codon between the C-terminal Nrf2 fragment and the detectable moiety. In some embodiments, the C-terminal Nrf2 fragment further comprises one or more mutations, substitutions, deletions, variants or combinations thereof. In other embodiments, the C-terminal fragment (Seg3) of Nuclear factor-erythroid 2 related factor 2 (Nrf2) is set forth in SEQ ID NO: 2, mutants or fragments thereof. In other embodiments, an isolated nucleic acid or cDNA sequence is at least about 50% in sequence identity to the sequence set forth as SEQ ID NO: 3. In other embodiments, the isolated nucleic acid is set forth in SEQ ID NO: 3 or cDNA sequences thereof.

In another embodiment, the nucleic acid can be DNA that encodes the mRNA. In this embodiment, the polynucleotide comprises promoter sequence(s) necessary for transcription of the C-terminal fragment (Seg3) of Nuclear factor-erythroid 2 related factor 2 (Nrf2) mRNA. Transcription promoter sequences and mRNA translation initiation sequences are well known in the art.

In another embodiment, an isolated peptide encoded by a nucleic acid sequence comprises a C-terminal fragment (Seg3) of Nuclear factor-erythroid 2 related factor 2 (Nrf2) operably linked to a detectable moiety.

In another embodiment, a method of screening for agents which modulate translation of Nuclear factor-erythroid 2 related factor 2 (Nrf2) comprises contacting a biosensor molecule with an agent wherein the biosensor molecule comprises an isolated nucleic acid or cDNA sequence of a C-terminal fragment (Seg3) of Nuclear factor-erythroid 2 related factor 2 (Nrf2) operably linked to a detectable moiety, and at least one stop codon between the C-terminal Nrf2 fragment and the detectable moiety; assessing the level of translation of the biosensor in the absence of a candidate agent to obtain a reference level of translation, assessing the level of translation of the biosensor in the presence of the candidate agent to obtain a test level of translation, wherein the candidate agent is identified as an agent that increases translation if the test level of translation is greater than the reference level of translation.

In some embodiments, a therapeutic agent comprises an agent identified by the methods embodied herein. In some embodiments, a pharmaceutical composition comprises one or more therapeutic agents.

In some embodiments, a method of treating a patient suffering from a disease, disorder or injury associated with reactive oxygen species (ROS) comprising administering to a patient a therapeutically effective amount of an agent which modulates the translation of a Nuclear factor-erythroid 2 related factor 2 (Nrf2) molecule wherein the agent has been identified by a method comprising, contacting a biosensor molecule with the agent wherein the biosensor molecule comprises an isolated nucleic acid or cDNA sequence of a C-terminal fragment (Seg3) of Nuclear factor-erythroid 2 related factor 2 (Nrf2) operably linked to a detectable moiety, and at least one stop codon between the C-terminal Nrf2 fragment and the detectable moiety; assessing the level of translation of the biosensor in the absence of the agent to obtain a reference level of translation, assessing the level of translation of the biosensor in the presence of the agent to obtain a test level of translation, wherein the agent is identified as an agent that modulates translation if the test level of translation is greater than the reference level of translation.

In one embodiment, a vector comprises a nucleic acid molecule encoding a C-terminal fragment (Seg3) of Nuclear factor-erythroid 2 related factor 2 (Nrf2), cDNA, mutants, variants or fragments thereof.

In another embodiment, a vector comprises an isolated nucleic acid or cDNA encoding a C-terminal fragment (Seg3) of Nuclear factor-erythroid 2 related factor 2 (Nrf2), a detectable moiety and at least one stop codon between the C-terminal Nrf2 fragment and the detectable moiety.

In another embodiment, an isolated cell comprises a C-terminal fragment (Seg3) of Nuclear factor-erythroid 2 related factor 2 (Nrf2) molecule, cDNA, mutants, variants or fragments thereof.

In some embodiments, an expression vector encodes a C-terminal fragment (Seg3) of Nuclear factor-erythroid 2 related factor 2 (Nrf2) or cDNA thereof. In some embodiments, the C-terminal fragment (Seg3) of Nuclear factor-erythroid 2 related factor 2 (Nrf2) comprises the sequence set forth as SEQ ID NO: 2, cDNA, mutants, variants, complementary sequences, or fragments thereof. In some embodiments, the C-fragment (Seg3) of Nuclear factor-erythroid 2 related factor 2 (Nrf2) comprises the sequence set forth as SEQ ID NO: 4, cDNA, mutants, variants, complementary sequences, or fragments thereof. In some embodiments, the nucleic acid sequences comprise on or more synonym codon substitutions, deletions, or insertions. In other embodiments, an expression vector encodes a nucleic acid sequence comprising at least about 50% sequence identity to SEQ ID NO: 3. In other embodiments, the nucleic acid sequence comprises at least about 75%, 80%, 85%, 90%, 95%, 96%, 97%, 98%, 99% sequence identity to SEQ ID NO: 3. In other embodiments, the nucleic acid sequence is set forth as SEQ ID NO: 3 or cDNA sequences thereof.

Other aspects are described infra.

BRIEF DESCRIPTION OF THE DRAWINGS

FIG. 1A is a blot showing that the overexpression of a construct containing the full length open reading frame of Nrf2 is limited. FIG. 1B is a schematic representation depicting three recombinant fragments that encompass the full length Nrf2 to independently evaluate their translation and expression levels. FIG. 1C is a blot showing the results from a semi quantitative RT-PCR of the three fragments (Seg1, Seg2, Seg3) to confirm their transcription after transfection. FIG. 1D is a Western blot showing the detection of the translation of the three recombinant fragments. The fragment Seg2 is highly over-expressed compared to fragments Seg1 and Seg3. The reduced expression of Nrf2 in the Seg1 can be explained by the presence of Keap1 binding site in this segment. Keap1 constitutively targets Nrf2 for ubiquitin-dependent proteosomal degradation under basal conditions. This effect of Keap1 on Nrf2 is confirmed by treating transfected cells with an inhibitor of proteasomal degradation (MG132) to prevent the degradation. Surprisingly, the Seg3 expression is repressed even more tightly than Seg1 and cannot be rescued by MG132. This data strongly support the presence of a translational repressor mechanism in Seg3. FIG. 1E is a blot. The translational repression mechanism in Seg3 prevents the translation of the highly expressed fragment Seg2. The effect of fusing either Seg1 or Seg3 with the highly expressed fragment Seg2 was evaluated. The construct with both the fragments 1 and 2 (Seg1-2) can be only overexpressed when the cells are exposed to MG132. On the contrary, the expression of the construct with fragments 2 and 3 (Seg2-3) cannot be rescued, even after proteosomal degradation is inhibited, indicating that the translational repression mechanism in the Sg3 can prevent the expression of sequences with good translation potential.

FIG. 2A is a diagram depicting embodiments of the constructs designed to evaluate the role of Seg3 in repressing the expression of eGFP. A stop codon was inserted between the reporter gene and Seg2 or Seg3 fragment in order to eliminate the effects mediated by protein degradation directed against the polypeptide encoded by these sequences. Addition of Seg3 to eGFP dramatically represses the expression eGFP. Conversely, Seg2 had no effect on the translation of eGFP. This data indicates that the Seg3 translational control mechanism only requires the presence of the mRNA sequence of this fragment in order to prevent the translation of the whole transcript. FIG. 2A discloses “6 His” as SEQ ID NO: 5.

FIG. 3A is a schematic representation showing that the sequence of the firefly luciferase reporter gene was fused with the Seg3 fragment to create a translation reporter system i.e. a biosensor for Nrf2. FIG. 3B is a graph showing the identification of compounds that increase the translation of luciferase under translational control mediated by Seg3. A small library of 127 compounds containing more than 80 known antioxidants was screened to identify potential activators of Nrf2 translation. Apigenin, a flavonoid, resveratrol and two analogs of resveratrol increased the translation of the Luciferase Reporter under translational control mediated by Sg3. FIG. 3C is a blot showing confirmation that the identified compounds can promote an increase in the translation of the entire Nrf2 ORF mRNA. HEK 293T cells were transfected with a construct a Nrf2 lacking amino acids 17-32 to prevent the degradation mediated by Keap1. The evaluation of the translation of this construct upon exposure to apigenin, resveratrol, amino resveratrol sulfate and triacetyl-resveratrol identified these as potent inducers of Nrf2 translation. Interestingly, the indirect inhibitors of Keap1-Nrf2 interaction i.e. TBHQ, EGG and sulforaphane had no effect on Nrf2 translation. Collectively, these data show for the first time the identification of direct modulators of Nrf2 protein expression.

FIG. 7A: eGFP fluorescence detection by laser scanning to evaluate the expression eGFP derived from recombinant constructs that contained the sequence of wild type Nrf2 segment 3 or the mutant with synonym codon substitutions. FIG. 7B: Evaluation of recombinant expression of wild type Nrf2 vs. a full length Nrf2 where the sequence corresponding to segment 3 was mutated using the synonym codons described in FIG. 7A. The bar graph to compare the signal intensity of the expression of this two constructs after laser scanning densitometry.

DETAILED DESCRIPTION

Figure 1A:
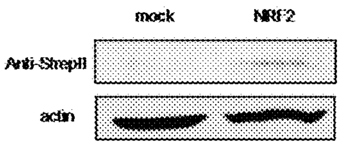
FIGS. 1A-1E show the identification of the Nrf2 translational repression domain. The expression of Nrf2 is regulated by a translational control mechanism located in the C-terminal of the main open reading frame.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events.

All genes, gene names, and gene products disclosed herein are intended to correspond to homologs and complementary DNA (cDNA) sequences from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "determining", "measuring", "evaluating", "detecting", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

"Optional" or "optionally" means that the subsequently described circumstance may or may not occur, such that the description includes instances where the circumstance occurs and instances where it does not.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive promoter" is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

As used herein "Nrf2" and "Nuclear factor (erythroid-derived 2)-like 2" are inclusive of all family members, mutants, cDNA sequences, alleles, fragments, species, coding and noncoding sequences, sense and antisense polynucleotide strands, etc.

An "isolated nucleic acid or cDNA" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs, and refers to nucleic acid sequences in which one or more introns have been removed. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, for instance, DNA which is part of a hybrid gene encoding additional polypeptide sequences.

A "polynucleotide" means a single strand or parallel and anti-parallel strands of a nucleic acid. Thus, a polynucleotide may be either a single-stranded or a double-stranded nucleic acid.

Unless otherwise indicated, the terms "peptide", "polypeptide" or "protein" are used interchangeably herein, although typically they refer to peptide sequences of varying sizes.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as "encoding" the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA (Eguchi et al., (1991) *Ann. Rev. Biochem.* 60, 631-652). An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

RNA interference "RNAi" is mediated by double stranded RNA (dsRNA) molecules that have sequence-specific homology to their "target" nucleic acid sequences (Caplen, N. J., et al. (2001) *Proc. Natl. Acad. Sci. USA* 98:9742-9747). In certain embodiments of the present invention, the mediators are 5-25 nucleotide "small interfering" RNA duplexes (siRNAs). The siRNAs are derived from the processing of dsRNA by an RNase enzyme known as Dicer (Bernstein, E., et al. (2001) *Nature* 409:363-366). siRNA duplex products are recruited into a multi-protein siRNA complex termed RISC(RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al. (2001) Nature 409:363-366; Boutla, A., et al. (2001) Curr. Biol. 11:1776-1780). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

"Analogs" in reference to nucleotides includes synthetic nucleotides having modified base moieties and/or modified sugar moieties (see e.g., described generally by Scheit, Nucleotide Analogs, John Wiley, New York, 1980; Freier & Altmann, (1997) *Nucl. Acid. Res.,* 25(22), 4429-4443, Toulme, J. J., (2001) *Nature Biotechnology* 19:17-18; Manoharan M., (1999) *Biochemica et Biophysica Acta* 1489:117-139; Freier S. M., (1997) *Nucleic Acid Research,* 25:4429-4443, Uhlman, E., (2000) *Drug Discovery & Development,* 3: 203-213, Herdewin P., (2000) *Antisense & Nucleic Acid Drug Dev.,* 10:297-310); 2'-O, 3'-C-linked [3.2.0] bicycloarabinonucleosides (see e.g. N. K Christiensen., et al, (1998) *J. Am. Chem. Soc.,* 120: 5458-5463; Prakash T P, Bhat B. (2007) *Curr Top Med. Chem.* 7(7):641-9; Cho E J, et al. (2009) *Annual Review of Analytical Chemistry,* 2, 241-264). Such analogs include synthetic nucleotides designed to enhance binding properties, e.g., duplex or triplex stability, specificity, or the like.

The term "variant," when used in the context of a polynucleotide sequence, may encompass a polynucleotide sequence related to a wild type or "native" gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

By "encoding" or "encoded", "encodes", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

The terms "patient", "subject" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. As used herein, "ameliorated" or "treatment" refers to a symptom which approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. For example, the term "treat" or "treating" with respect to tumor cells refers to stopping the progression of said cells, slowing down growth, inducing regression, or amelioration of symptoms associated with the presence of said cells. Treatment of an individual suffering from an infectious disease organism refers to a decrease and elimination of the disease organism from an individual. For example, a decrease of viral particles as measured by plaque forming units or other automated diagnostic methods such as ELISA etc.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention.

As defined herein, a "therapeutically effective amount" of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

As used herein, the term "reporter gene" refers to a coding sequence attached to heterologous promoter or enhancer elements and whose product may be assayed easily and quantifiably when the construct is introduced into tissues or cells. An example of a "reporter gene" is a nucleic acid encoding a reporter enzyme, i.e., a catalytic product that mediates a reaction of a substrate that produces a detectable signal.

Compositions

Nuclear factor-erythroid 2 related factor 2 (Nrf2) is a transcription factor that regulates the gene expression of a wide variety of cytoprotective phase II detoxification and antioxidant enzymes. Under basal conditions Nrf2 is bound to Kelch like ECH-associated protein 1 (Keap1) also known as cytoplasmic inhibitor (INrf2). Keap1 functions as an adaptor for Cul3/Rbx1 mediated ubiquitination and proteosomal degradation of Nrf2. Hence cytoplasmic Nrf2 levels are maintained at very low levels. Upon exposure to environmental [e.g. xenobiotics, UV etc) and endogenous stressors (e.g. ROS), both Keap1 and Nrf2 are post translationally modified and dissociate from each other. Phosporylated Nrf2 then translocates to the nucleus and bind to an enhancer sequence known as the antioxidant-responsive element (ARE) together with either Jun or small MAF. ARE is a promoter element found in many antioxidant enzymes, including superoxide dismutase (SOD), peroxiredoxins, thioredoxins, catalase, glutathione peroxidase, and heme oxygenase-1 (HO-1). Nrf2, therefore, plays a pivotal role in the ARE-driven cellular defense system against oxidative stress. The protective role of Nrf2 activation has also been established in numerous human diseases including cancer, chronic obstructive pulmonary disease (COPD), Parkinson's disease, Alzheimer's disease, diabetes, asthma, heart diseases, atherosclerosis, inflammatory bowel disease, multiple sclerosis, osteoarthritis, and rheumatoid arthritis. Regulation of Nrf2 has also been implicated in the determination of health span, longevity, and aging. This has made agents that act on the Nrf2 or keap1 of great scientific interest for their possible use as therapeutic agents. It is noteworthy that most of the currently known activators of antioxidants ARE, are indirect inhibitors of Nrf2-Keap1 interaction and they are believed to form covalent adducts with the sulfhydryl groups of cysteines in Keap1 by oxidation or alkylation.

Accordingly, identifying therapeutic agents for treatment of diseases associated with Nrf2 and associated molecules and pathways thereof, would be of great benefit.

In general embodiments, compositions comprise nucleic acid sequences of Nuclear factor (erythroid-derived 2)-like 2 (Nrf2), including without limitation, cDNA, sense and/or antisense sequences of NRF2.

In some embodiments, a biosensor comprises an isolated nucleic acid or cDNA sequence or synthetic nucleic acid sequence, encoding a C-terminal fragment (Seg3) of Nuclear factor-erythroid 2 related factor 2 (Nrf2) operably linked to a detectable moiety. The term "nucleic acid sequence" will be used for the sake of brevity and will include, without limitation, isolated nucleic acid or cDNA sequences, synthesized or synthetic nucleic acid sequences, chimeric nucleic acid sequences, homologs, orthologs, variants, mutants or combinations thereof. The detectable moiety can be, for example, a reporter gene.

Examples of reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy, Fluorescence Activated Cell Sorting (FACS), fluorescence microscopy), antibiotic resistance determination.

In some embodiments, the biosensor comprises at least about a 50% sequence identity to SEQ ID NO: 2 or cDNA sequences thereof. In other embodiments, the biosensor comprises at least about 75%, 80%, 85%, 90%, 95%, 96%, 97%, 98%, 99% sequence identity to SEQ ID NO: 2 or cDNA sequences thereof. In other embodiments, the biosensor sequence is set forth as SEQ ID NO: 2 or cDNA sequences thereof.

In some embodiments, the biosensor comprises at least about a 50% sequence identity to SEQ ID NO: 3 or cDNA sequences thereof. In other embodiments, the biosensor comprises at least about 75%, 80%, 85%, 90%, 95%, 96%, 97%, 98%, 99% sequence identity to SEQ ID NO: 3 or cDNA sequences thereof. In other embodiments, the biosensor sequence is set forth as SEQ ID NO: 3 or cDNA thereof.

In some embodiments, the biosensor comprises at least about a 50% sequence identity to SEQ ID NO: 4 or cDNA sequences thereof. In other embodiments, the biosensor comprises at least about 75%, 80%, 85%, 90%, 95%, 96%, 97%, 98%, 99% sequence identity to SEQ ID NO: 4 or cDNA sequences thereof. In other embodiments, the biosensor sequence is set forth as SEQ ID NO: 4 or cDNA sequences thereof.

In other embodiments, the biosensors comprises one or more synonym codon substitutions.

In embodiments, the nucleic acid sequence or cDNA sequences thereof comprises at least one stop codon between the C-terminal Nrf2 fragment and the detectable moiety.

Figure 2A:
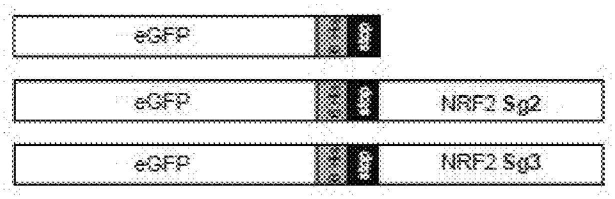
FIGS. 2A and 2B show that the Seg3 mediated translational repression mechanism inhibits the expression of a reporter gene (eGFP).

In some embodiments, the C-terminal Nrf2 fragment (Seg3) or cDNA sequences thereof, and the detectable moiety optionally comprise one or more linker molecules. For example, the linker molecules can be positioned between the Seg3 and the detectable moiety. The detectable moiety can be fused, or linked directly or indirectly at the 5' or 3' end of the Seg3. See, for example, FIGS. 2A, 3A.

In embodiments, the detectable moiety comprises: a luminescent moiety, a chemiluminescent moiety, a fluorescence moiety, a bioluminescent moiety, an enzyme, a natural or synthetic moiety. In some embodiments, the detectable moiety is selected from the group consisting of luciferase and fluorescent protein.

In some embodiments, the nucleic acid sequence comprises: a C-terminal fragment (Seg3) of Nuclear factor-erythroid 2 related factor 2 (Nrf2) or cDNA sequences thereof, operably linked to a detectable moiety and at least one stop codon between the C-terminal Nrf2 fragment and the detectable moiety. In some embodiments, the C-terminal Nrf2 fragment and the detectable moiety optionally comprise one or more linker molecules linking the Seg3 of Nrf2 and the detectable moiety.

In embodiments, the C-terminal Nrf2 fragment further comprises one or more mutations, substitutions, deletions, variants or combinations thereof.

In some embodiments, the nucleic acid sequence comprises at least about 50% sequence identity to SEQ ID NO: 3 or cDNA sequences thereof. In other embodiments, the nucleic acid sequence comprises at least about 75%, 80%, 85%, 90%, 95%, 96%, 97%, 98%, 99% sequence identity to SEQ ID NO: 3, or cDNA sequences thereof. In other embodiments, the nucleic acid sequence is set forth as SEQ ID NO: 3 or cDNA sequences thereof.

In another preferred embodiment, the nucleic acid sequence encodes a C-terminal fragment (Seg3) of Nuclear factor-erythroid 2 related factor 2 (Nrf2) or cDNA sequences thereof. In some embodiments, the C-fragment (Seg3) of Nuclear factor-erythroid 2 related factor 2 (Nrf2) comprises the sequence set forth as SEQ ID NO: 2, mutants, variants, complementary sequences, fragments or cDNA sequences thereof.

In some embodiments, the homology, sequence identity or complementarity, between the C-terminal fragment (Seg3) of Nuclear factor-erythroid 2 related factor 2 (Nrf2) nucleic acid and the native or wild type or cDNA sequences of C-terminal fragment (Seg3) of Nuclear factor-erythroid 2 related factor 2 (Nrf2) is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In one embodiment, an expression vector encodes a C-terminal fragment (Seg3) of Nuclear factor-erythroid 2 related factor 2 (Nrf2) or cDNA sequences thereof. In some embodiments, the C-fragment (Seg3) of Nuclear factor-erythroid 2 related factor 2 (Nrf2) comprises the sequence set forth as SEQ ID NO: 2, cDNA, mutants, variants, complementary sequences, fragments thereof. In one embodiment, the an expression vector encodes a nucleic acid sequence comprising at least about 50% sequence identity to SEQ ID NO: 3 or cDNA sequences thereof. In other embodiments, the nucleic acid sequence comprises at least about 75%, 80%, 85%, 90%, 95%, 96%, 97%, 98%, 99% sequence identity to SEQ ID NO: 3 or cDNA sequences thereof. In other embodiments, the nucleic acid sequence is set forth as SEQ ID NO: 3 or cDNA sequences thereof.

Modified Nucleic Acid Sequences:

It is not intended that the present invention be limited by the nature of the nucleic acid employed. The target nucleic acid may be native, synthesized nucleic acid, or a combination thereof. The nucleic acid may be partially or wholly from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996*, J. Biol. Chem.* 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as pGEM® T vector or SP65 (Promega Corporation, Madison, Wis.).

Accordingly, certain preferred nucleic acid sequences of this invention are chimeric nucleic acid sequences. "Chimeric nucleic acid sequences" or "chimeras," in the context of this invention, contain two or more chemically distinct regions, each made up of at least one nucleotide. These sequences typically contain at least one region of modified nucleotides that confers one or more beneficial properties (such as, for example, increased nuclease resistance, increased uptake into cells, increased binding affinity for the target)

Chimeric nucleic acid sequences of the invention may be formed as composite structures of two or more oligonucleotides, modified oligonucleotides, oligonucleosides and/or oligonucleotide mimetics. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

Specific examples of some modified nucleic acid sequences envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Examples of oligonucleotides with phosphorothioate backbones and those with heteroatom backbones, include without limitation: $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH,). The amide backbones disclosed by De Mesmaeker et al. (1995) *Acc. Chem. Res.* 28:366-374 are also one example. In other embodiments, a nucleic acid sequence comprises morpholino backbone structures (Summerton and Weller, U.S. Pat. No. 5,034,506). In other embodiments, such as the peptide nucleic acid (PNA) backbone, the phosphodiester backbone of the nucleic acid sequence is replaced with a polyamide backbone, the nucleotides being bound directly or indirectly to the aza nitrogen atoms of the polyamide backbone (Nielsen et al. (1991) *Science* 254, 1497). Nucleic acid sequences may also comprise one or more substituted sugar moieties. Examples include: OH, SH, $SCH_3$, F, OCN, $OCH_3OCH_3$, OCH3O$(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a reporter group; an intercalator; a group for improving the pharmacokinetic properties of an oligonucleotide; or a group for improving the pharmacodynamic properties of an oligonucleotide and other substituents having similar properties. Other modifications include, for example: 2'-methoxyethoxy [2'-O—$CH_2CH_2OCH_3$, also known as 2'-O-(2-methoxyethyl)] (Martin et al., (1995) *Helv. Chim. Acta,* 78, 486), 2'-methoxy (2'-O—$CH_3$), 2'-propoxy (2'-$OCH_2CH_2CH_3$) and 2'-fluoro (2'-F). Similar modifications may also be made at any positions on the oligonucleotide, the 2' or the 3' position of the sugar on the 3' terminal nucleotide and the 5' position of 5' terminal nucleotide. The nucleic acid sequences may also have sugar mimetics such as cyclobutyls in place of the pentofuranosyl group.

Preferred modified oligonucleotide backbones comprise, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

The nucleic acid sequences may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. (Kornberg, A., DNA Replication, W.H. Freeman & Co., San Francisco, 1980, pp 75-77; Gebeyehu, G., (1987) et al. *Nucl. Acids Res.* 15:4513). A "universal" base known in the art, e.g., inosine, may be included.

Another modification involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, cholic acid, a thioether, e.g., hexyl-5-tritylthiol, a, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid. Nucleic acid sequences comprising lipophilic moieties, and methods for preparing such oligonucleotides are known in the art, for example, U.S. Pat. Nos. 5,138,045, 5,218,105 and 5,459,255.

It is not necessary for all positions in a given nucleic acid sequence to be uniformly modified, and in fact more than one of the aforementioned modifications may be incorporated in a single nucleic acid sequence or even at within a single nucleoside within an such sequences. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

In another embodiment, the nucleic acid sequences comprise one or more nucleotides substituted with locked nucleic acids (LNA). The LNA modified nucleic acid sequences may have a size similar to the parent or native sequence or may be larger or preferably smaller. It is preferred that such LNA-modified oligonucleotides contain less than about 70%, more preferably less than about 60%, most preferably less than about 50% LNA monomers and that their sizes are between about 1 and 25 nucleotides.

Peptides:

In another embodiment, an isolated peptide encoded by a nucleic acid comprises a C-terminal fragment (Seg3) of Nuclear factor-erythroid 2 related factor 2 (Nrf2) or cDNA sequences thereof. The peptide can also be a synthetic peptide of the C-terminal fragment of (Seg3) of Nuclear factor-erythroid 2 related factor 2 (Nrf2).

In other embodiments, an isolated peptide encoded by a nucleic acid sequence comprises a C-terminal fragment (Seg3) of Nuclear factor-erythroid 2 related factor 2 (Nrf2) operably linked to a detectable moiety.

It is to be understood that the peptide sequences are not limited to the native or cDNA sequences thereof, of Nrf2. The skilled artisan will recognize that conservative amino acid changes may be made, which although they alter the primary sequence of the protein or peptide, do not normally alter its function. Conservative amino acid substitutions typically include substitutions within the following groups: glycine, alanine, valine, isoleucine, leucine; aspartic acid, glutamic acid, asparagine, glutamine, serine, threonine, lysine, arginine, phenylalanine, tyrosine.

Conservative substitutions may also be made based on types of amino acids: aliphatic (valine, isoleucine, leucine, and alanine); charged (aspartic acid, glutamic acid, lysine, arginine, and histidine); aromatic residues (phenylalanine, tyrosine and tryptophan); and sulfur-containing (methionine and cysteine). Polypeptide sequences having at least about 68% identity, at least about 70% identity, or at least about 71% identity to Nrf2, the C-terminal fragment of Nrf2 (Seg3), or cDNA sequences thereof, or those peptides encoded by SEQ ID NO: 1 or 2 SEQ ID No. 1 or cDNA sequences thereof are also embodied herein.

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) can be used. In calculating percent identity, exact matches are typically counted.

Also included in the invention are polynucleotides encoding hybrid proteins comprising a C-terminal fragment of Nrf2 polypeptide or fragment thereof operatively fused directly or indirectly via peptide linker, to a second polypeptide sequence. Linker sequences are well known in the art. "C-terminal fragment of Nrf2" or "Seg3 fragment" in the practice of the invention refers to a fragment comprising at least 1 to 10 amino acids encoded by SEQ ID No. 2 or cDNA sequences thereof. In a preferred embodiment, a hybrid protein comprises a Seg3 of Nrf2 polypeptide or fragment thereof operatively fused to a detectable moiety, such as, a reporter polypeptide, wherein the reporter polypeptide is fused to the N- or C-terminal of the Seg3 polypeptide, directly or indirectly. Exemplary reporter polypeptides include luciferase (LUC), green fluorescent protein (GFP), and GFP derivatives.

Hybrid proteins comprising a Seg3 polypeptide or fragment thereof may be linked to other types of polypeptides, in addition to a reporter polypeptide, or in lieu of a reporter polypeptide. These additional polypeptides may be any amino acid sequence useful for the purification, identification and/or therapeutic or prophylactic application of the peptide. Non-limiting examples of such additional segments include LacZ, FLAG-tag, Myc, His6 and the like. The Seg3 polypeptide portion may be fused directly to the second peptide or may be separated by a linker sequence.

Candidate Agents and Screening Assays

The compositions embodied herein, can also be applied in the areas of drug discovery and target validation. The present invention comprehends the use of the nucleic acid sequences and peptides embodied herein, in drug discovery efforts to elucidate relationships that exist between Nuclear factor (erythroid-derived 2)-like 2 (NRF2) polynucleotides and a disease state, phenotype, or condition. These methods include detecting or modulating Nuclear factor (erythroid-derived 2)-like 2 (NRF2) polynucleotides comprising contacting a sample, tissue, cell, or organism with a compound, measuring the nucleic acid or protein level of Nuclear factor (erythroid-derived 2)-like 2 (NRF2) polynucleotides and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

The screening assays of the invention suitably include and embody, animal models, cell-based systems and non-cell based systems. The nucleic acid sequences and peptides embodied herein, are used for identifying agents of therapeutic interest, e.g. by screening libraries of compounds or otherwise identifying compounds of interest by any of a variety of drug screening or analysis techniques, or synthesis of novel compounds. The gene, allele, fragment, or oligopeptide thereof employed in such screening may be free in solution, affixed to a solid support, borne on a cell surface, or located intracellularly. The measurements are conducted as described in detail in the examples section which follows. In embodiments, screening candidate agents is performed to identify those which modulate the translation of Nrf2.

The assays can be of an in vitro or in vivo format. In vitro formats of interest include cell-based formats, in which contact occurs e.g., by introducing the substrate in a medium, such as an aqueous medium, in which the cell is present. In yet other embodiments, the assay may be in vivo, in which a multicellular organism that includes the cell is employed. Contact of a targeting vector encoding the nucleic acid sequences embodied herein, with the target cell(s) may be accomplished using any convenient protocol. In those embodiments where the target cells are present as part of a multicellular organism, e.g., an animal, the vector is conveniently administered to (e.g., injected into, fed to, etc.) the multicellular organism, e.g., a whole animal, where administration may be systemic or localized, e.g., directly to specific tissue(s) and/or organ(s) of the multicellular organism.

Multicellular organisms of interest include, but are not limited to: insects, vertebrates, such as avian species, e.g., chickens; mammals, including rodents, e.g., mice, rates; ungulates, e.g., pigs, cows, horses; dogs, cats, primates, e.g., monkeys, apes, humans; and the like. As such, the target cells of interest include, but are not limited to: insects cells, vertebrate cells, particularly avian cells, e.g., chicken cells; mammalian cells, including murine, porcine, ungulate, ovine, equine, rat, dog, cat, monkey, and human cells; and the like.

The target cell comprising the biosensor is contacted with a test compound and the translation of the biosensor is evaluated or assessed by detecting the presence or absence of signal from a detectable moiety, for example, luciferase substrate, i.e., by screening the cell (either in vitro or in vivo) for the presence of a luciferase mediated luminescent signal. The detected signal is then employed to evaluate the translational activity of a biosensor in the presence of a test agent.

The luminescent signal may be detected using any convenient luminescent detection device. In certain embodiments, detectors of interest include, but are not limited to: photo-multiplier tubes (PMTs), avalanche photodiodes (APDs), charge-coupled devices (CCDs); complementary metal oxide semiconductors (CMOS detectors) and the like. The detector may be present in a signal detection device, e.g., luminometer, which is capable of detecting the signal once or a number of times over a predetermined period, as desired. Data may be collected in this way at frequent intervals, for example once every 10 ms, over the course of a given assay time period.

In certain embodiments, the subject methods are performed in a high throughput (HT) format. In the subject HT embodiments of the subject invention, a plurality of different cells are simultaneously assayed or tested. By simultaneously tested is meant that each of the cells in the plurality are tested at substantially the same time. In general, the number of cells that are tested simultaneously in the subject HT methods ranges from about 10 to 10,000, usually from about 100 to 10,000 and in certain embodiments from about 1000 to 5000. A variety of high throughput screening assays for determining the activity of candidate agent are known in the art and are readily adapted to the present invention, including those described in e.g., Schultz (1998) *Bioorg Med Chem Lett* 8:2409-2414; Fernandes (1998) *Curr Opin Chem Biol* 2:597-603; as well as those described in U.S. Pat. No. 6,127,133; the disclosures of which are herein incorporated by reference.

In some embodiments, a method of screening for agents which modulate translation of Nuclear factor-erythroid 2 related factor 2 (Nrf2) comprises contacting a biosensor molecule with an agent wherein the biosensor molecule comprises an isolated nucleic acid or cDNA sequence of a C-terminal fragment (Seg3) of Nuclear factor-erythroid 2 related factor 2 (Nrf2) operably linked to a detectable moiety, and at least one stop codon between the C-terminal Nrf2 fragment and the detectable moiety; assessing the level of translation of the biosensor in the absence of a candidate agent to obtain a reference level of translation, assessing the level of translation of the biosensor in the presence of the candidate agent to obtain a test level of translation, wherein the candidate agent is identified as an agent that increases translation if the test level of translation is greater than the reference level of translation.

In embodiments, the detectable moiety comprises: a luminescent moiety, a chemiluminescent moiety, a fluorescence moiety, a bioluminescent moiety, an enzyme, a natural or synthetic moiety.

In some embodiments, the agent inhibits translation of the Nrf2 with respect to a reference level of translation.

In some embodiments, a method of screening for agents which modulate translation of Nuclear factor-erythroid 2 related factor 2 (Nrf2) comprises contacting a biosensor molecule with an agent wherein the biosensor molecule comprises an isolated nucleic acid sequence set forth in SEQ ID NO: 2, cDNA sequences or fragments thereof, operably linked to a detectable moiety, and at least one stop codon between the sequence set forth in SEQ ID NO: 2, fragments or cDNA sequences thereof and the detectable moiety; assessing the level of translation of the biosensor in the absence of a candidate agent to obtain a reference level of translation, assessing the level of translation of the biosensor in the presence of the candidate agent to obtain a test level of translation, wherein the candidate agent is identified as an agent that increases translation if the test level of translation is greater than the reference level of translation.

Any method known in the art can be used to assess translation. In a preferred embodiment, translation is assessed using mammalian cells transfected with an expression vector comprising a nucleic acid of the invention. The transfection may be transient or the cells may stably transformed with the expression vector. A cell-based assay such as described in Butcher et al., 2007, *J Biol Chem.* 282:2853-28539 may be used. Alternatively, an in vitro translation assay may be used.

In the context of an expression vector, the vector can be readily introduced into a host cell, e.g., mammalian, bacterial, yeast or insect cell, by any method in the art. For example, the expression vector can be transferred into a host cell by physical, chemical or biological means.

Physical methods for introducing a polynucleotide into a host cell include calcium phosphate precipitation, lipofection, particle bombardment, microinjection, electroporation, photoporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

In the case where a non-viral delivery system is utilized, a preferred delivery vehicle is a liposome. The above-mentioned delivery systems and protocols therefore can be found in "Gene Targeting Protocols, 2ed.", Kmiec ed., Humana Press, Totowa, N.J., pp 1-35 (2002) and "Gene Transfer and Expression Protocols, Vol. 7, (Methods in Molecular Biology)," Murray ed., Humana Press, Totowa, N.J., pp 81-89 (1991).

Candidate Agents:

The methods can be practiced with any test compounds as candidate agents. Test compounds useful in practicing the inventive method may be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, *Anticancer Drug Des.* 12:145).

Examples of methods for the synthesis of molecular libraries may be found in the art, for example, in: DeWitt et al., 1993, *Proc. Natl. Acad. Sci. USA* 90:6909-6913; Erb et al., 1994, *Proc. Natl. Acad. Sci. USA* 91:11422-11426; Zuckermann et al., 1994, *J. Med. Chem.* 37:2678-2685; Cho et al., 1992, *Science* 261:1303-1305; Carell et al., 1994, *Angew. Chem. Int. Ed. Engl.* 33:2059-2061; Carell et al., 1994, *Angew. Chem. Int. Ed. Engl.* 33:2061-2064; and Gallop et al., 1994, *J. Med. Chem.* 37:1233-1251.

Libraries of compounds may be presented in solution (e.g., Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223,409), plasmids (Cull et al., 1992, *Proc. Natl. Acad. Sci. USA* 89:1865-1869), or phage (Scott and Smith, 1990, *Science* 249:386-390; Devlin, 1990, *Science* 249:404-406; Cwirla et al., 1990, *Proc. Natl. Acad. Sci. USA* 87:6378-6382; and Felici, 1991, *J Mol. Biol.* 222:301-310).

Commercially available libraries that may be screened include, but are not limited to, the TimTec Natural Product Library (NPL), NPL-640, and TimTec NDL-3000 library. Libraries comprising compounds modeled on polyamines (i.e., polyamine analogs) may also be screened.

In certain embodiments, the candidate agent is a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The method may be practiced iteratively using different concentrations of a test candidate and/or different testing conditions, such as duration of reaction time. Test candidates that are identified by the method can be further tested by conventional methods in the art to verify specificity, dose dependency, efficacy in vivo, and the like. Test candidates may serve as lead compounds for developing additional test candidates.

As indicated above, the present invention finds use in monitoring translational activity of the biosensor in an assay wherein the test is conducted using cells. In these embodiments, the cells are cultured under specific user-defined conditions (e.g., in the presence or absence of a cytokine, nutrient and/or candidate therapeutic agent), and monitored for emitted light.

A prototype compound may be believed to have therapeutic activity on the basis of any information available to the artisan. For example, a prototype compound may be believed to have therapeutic activity on the basis of information contained in the Physician's Desk Reference. In addition, by way of non-limiting example, a compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases.

A therapeutically-active compound is a compound that has therapeutic activity, including for example, the ability of a compound to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder associated with damage by reactive oxygen intermediates. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate compounds can be isolated, from microorganisms, animals or plants, for example, and can be produced recombinantly, or synthesized by chemical methods known in the art. If desired, candidate compounds of the present invention can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries. The other four approaches are applicable to polypeptide, non-peptide oligomers, or small molecule libraries of compounds and are preferred approaches in the present invention. See Lam, *Anticancer Drug Des.* 12: 145-167 (1997).

In an embodiment, the present invention provides a method of identifying a candidate compound as a suitable prodrug. A suitable prodrug includes any prodrug that may be identified by the methods of the present invention. Any method apparent to the artisan may be used to identify a candidate compound as a suitable prodrug.

In another aspect, the present invention provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In an embodiment, a method of screening candidate compounds for suitability as therapeutic agents is provided, where the method comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labeling, or LCMS.

In screening compounds for suitability as therapeutic agents, intracellular persistence of the candidate compound is evaluated. In a preferred embodiment, the agents are evaluated for their ability to modulate the translation of compositions embodied herein, over a period of time in response to a candidate therapeutic agent.

In another preferred embodiment, soluble and/or membrane-bound forms of compositions embodied herein, e.g. proteins, mutants or biologically active portions thereof, can be used in the assays for screening candidate agents. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON™ X-100, TRITON™ X-114, THESIT™, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays can also be used and involve preparing a reaction mixture which includes biosensor comprising a bioluminescent moiety and the test compound under conditions and time periods to allow the measurement of the translational activity over time, and concentrations of test agents.

In other embodiments, a candidate agent is an antisense oligonucleotide. In embodiments, Nrf2 expression (e.g., protein) in a sample (e.g., cells or tissues in vivo or in vitro) treated using an antisense oligonucleotide of the invention is evaluated by comparison with Nrf2 expression in a control sample. For example, the translation of the Nrf2 is monitored by the signal emitted by the detectable moiety and compared with that in a mock-treated or untreated sample. Alternatively, comparison with a sample treated with a control antisense oligonucleotide (e.g., one having an altered or different sequence) can be made depending on the information desired. In another embodiment, a difference in the translational activity in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In some embodiments, the level of Nrf2 protein, in a sample treated with an antisense oligonucleotide, is increased or decreased by about 1.25-fold to about 10-fold or more relative to an untreated sample or a sample treated with a control nucleic acid. In embodiments, the level of Nrf2 protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Diagnostics, Therapeutics, Kits

The compositions herein and compounds of the present invention can be utilized for diagnostics, therapeutics, and prophylaxis, and as research reagents and components of kits.

As discussed, Nuclear factor erythroid 2-related factor 2 (Nrf2) is a redox-sensitive transcription factor that upregulates a battery of antioxidative genes and cytoprotective enzymes that constitute the defense against oxidative stress. Modulation of this polynucleotide is important in treatment of diseases or disorders that are associated with oxidative stress. Exemplary Nuclear factor (erythroid-derived 2)-like 2 (NRF2) mediated diseases and disorders which can be treated comprise: chronic obstructive pulmonary disease (COPD), multiple sclerosis, a hepatic disease or disorder, a gastrointestinal disease or disorder, diabetes, autoimmunity, an immune related disease or disorder, an immunodeficiency (e.g., AIDS), a neurological disease or disorder, a neurodegenerative disease or disorder, a disease or disorder or condition associated with oxidative stress, an eye disease (e.g., age-related macular degeneration, cataracts, light retinopathy, retinopathy of prematurity etc.), a skin disease, asthma, arteriosclerosis, a chronic inflammatory diseases or condition (e.g., vasculitis, pulmonary bronchitis, rheumatoid arthritis, osteoarthritis, hepatitis, pancreatitis, dermatitis, esophagitis, ulcerative colitis, Crohn's disease, conjunctivitis etc.), nerve repair and paralysis, neuroendocrine differentiation, an inflammatory disease, a muscular disease or disorder, diseases or disorders associated with infectious organisms, senile plaques, cerebral amyloid angiopathy, atherosclerosis, glioblastoma, amyloid deposition, neurofibrillary tangles, dementia, choriocarcinoma, astrocytoma, amyloidosis, hyperlipidemia, neoplastic transformation, an atherosclerotic plaque, an atherosclerotic obstruction, metastasis, myocardial infarction, pulmonary fibrosis, necrosis, shock, melanoma, colorectal carcinoma, genetic susceptibility, psoriasis, a disease or disorder associated with abnormal cell proliferation ((e.g., cancer, psoriasis etc.), cancer (e.g., prostate cancer, lung cancer, breast cancer, Non-small cell lung carcinomas (NSCLCs), leukemia etc.), inflammation, glioma, carcinoma, neuropathology, tumors, vascular diseases, cell damage, brain tumors, hypercholesterolemia, liposarcoma, coronary heart disease, coronary artery disease, glomerulonephritis, venous thrombosis and a pathological process.

In another preferred embodiment, the agents modulate the expression and/or function of Nrf2 in patients suffering from or at risk of developing diseases or disorders associated with molecules or pathways associated with Nrf2. Examples of such diseases or disorders associated comprise: Alzheimer's disease, multiple sclerosis, senile plaques, cerebral amyloid angiopathy, atherosclerosis, glioblastoma, amyloid deposition, neurodegenerative diseases, neurofibrillary tangles, dementia, choriocarcinoma, astrocytoma, amyloidosis, hyperlipidemia, neurodegeneration, neoplastic transformation, prostate cancer, atherosclerotic plaque, obstruction, AIDS, metastasis, myocardial infarction, pulmonary fibrosis, necrosis, shock, melanoma, colorectal carcinoma, genetic susceptibility, psoriasis, cancer, inflammation, glioma, carcinoma, breast cancer, neuropathology, tumors, prostate carcinoma, vascular diseases, cell damage, brain tumors, Non-small cell lung carcinomas (NSCLCs), hypercholesterolemia, liposarcoma, coronary heart disease, immunodeficiency, coronary artery disease, glomerulonephritis, venous thrombosis, pathological processes or leukemia.

As used herein, the term “cancer” refers to any malignant tumor, particularly arising in the lung, kidney, or thyroid. The cancer manifests itself as a “tumor” or tissue comprising malignant cells of the cancer. Examples of tumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing’s tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms’ tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

As used herein, the terms “cancer,” “neoplasm,” and “tumor,” are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a “clinically detectable” tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

In embodiments, the agents identified by the methods embodied herein, are administered to patients suffering from or at risk of developing a neurological disease or disorder. “Neurological disease or disorder” refers to any disease or disorder of the nervous system and/or visual system. “Neurological disease or disorder” include disease or disorders that involve the central nervous system (brain, brainstem and cerebellum), the peripheral nervous system (including cranial nerves), and the autonomic nervous system (parts of which are located in both central and peripheral nervous system). A neurological disease or disorder includes but is not limited to acquired epileptiform aphasia; acute disseminated encephalomyelitis; adrenoleukodystrophy; age-related macular degeneration; agenesis of the corpus callosum; agnosia; Aicardi syndrome; Alexander disease; Alpers’ disease; alternating hemiplegia; Alzheimer’s disease; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet’s disease; Bell’s palsy; benign essential blepharospasm; benign focal; amyotrophy; benign intracranial hypertension; Binswanger’s disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing’s syndrome; cytomegalic inclusion body disease; cytomegalovirus infection; dancing eyes-dancing feet syndrome; DandyWalker syndrome; Dawson disease; De Morsier’s syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb’s palsy; essential tremor; Fabry’s disease; Fahr’s syndrome; fainting; familial spastic paralysis; febrile seizures; Fisher syndrome; Friedreich’s ataxia; fronto-temporal dementia and other “tauopathies”; Gaucher’s disease; Gerstmann’s syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIV associated dementia and neuropathy (also neurological manifestations of AIDS); holoprosencephaly; Huntington’s disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh’s disease; Lennox-Gustaut syndrome; Lesch-Nyhan syndrome; leukodystrophy; Lewy body dementia; Lissencephaly; locked-in syndrome; Lou Gehrig’s disease (i.e., motor neuron disease or amyotrophic lateral sclerosis); lumbar disc disease; Lyme disease—neurological sequelae; Machado-Joseph disease; macrencephaly; megalencephaly; Melkersson- Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; a neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

In embodiments, a method of treating a patient suffering from a disease, disorder or injury associated with reactive oxygen species (ROS) comprises administering to a patient a therapeutically effective amount of an agent which modulates the translation of a Nuclear factor-erythroid 2 related factor 2 (Nrf2) molecule wherein the agent has been identified by a method comprising: contacting a biosensor molecule with the agent wherein the biosensor molecule comprises an isolated nucleic acid or cDNA sequence of a C-terminal fragment (Seg3) of Nuclear factor-erythroid 2 related factor 2 (Nrf2) operably linked to a detectable moiety, and at least one stop codon between the C-terminal Nrf2 fragment and the detectable moiety; assessing the level of translation of the biosensor in the absence of the agent to obtain a reference level of translation, assessing the level of translation of the biosensor in the presence of the agent to obtain a test level of translation, wherein the agent is identified as an agent that modulates translation if the test level of translation is greater than the reference level of translation.

In embodiments, the agent increases the level of translation of the Nrf2 molecule in vitro or in vivo. In some embodiments, the agent increases the level of translation by at least about 85%, or at least about 90%, or at least about 95%.

In some embodiments, an agent decreases the level of translation of the Nrf2 molecule in vitro or in vivo. In embodiments, the agent decreases the level of translation by at least about 85%, or at least about 90%, or at least about 95%.

In another embodiment, an agent modulates reactive oxygen species (ROS) levels in vitro or in vivo.

The compounds of the invention can be utilized in pharmaceutical compositions by adding an effective amount of a compound to a suitable pharmaceutically acceptable diluent or carrier. Use of the compounds and methods of the invention may also be useful prophylactically.

Kits of the invention comprise nucleic acid sequences or peptides embodied herein. These may be conjugated to a detectable moiety or the detectable moiety is included in the kit or obtained separately. In cases where the kit does not contain a detectable moiety or the moiety and the nucleic acids or peptides are not linked, instructions for carrying out the linking are provided.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Modulators of Nrf2

In search for direct modulators of Nrf2, the mechanism by which Nrf2 is expressed needed to be elucidated. The clues to uncovering the puzzle came from experiments described herein, that indicated that the recombinant overexpression of the reading frame of Nrf2 was very limited even if the segment that allows the Nrf2-Keap1 interaction was deleted from the mRNA sequence (FIG. 1A). According to the inventors' experience this was indicative of a potential novel translational control mechanism located in the ORF.

Figure 1B:
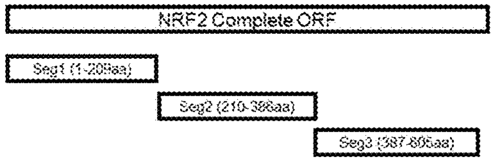
Figure 1C:
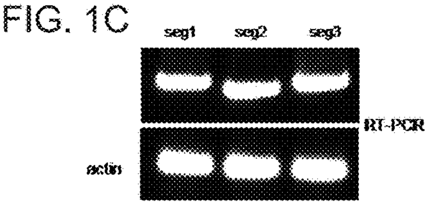
Figure 1D:
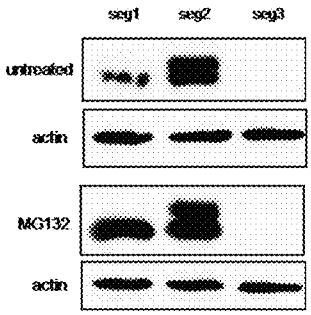
Figure 1E:
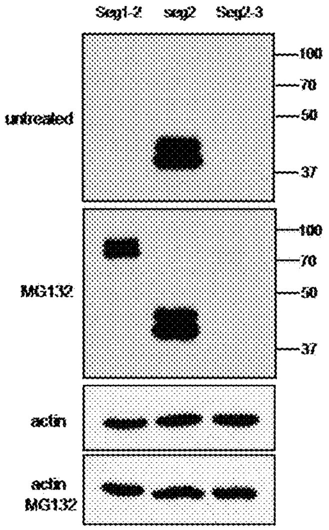
Figure 2B:
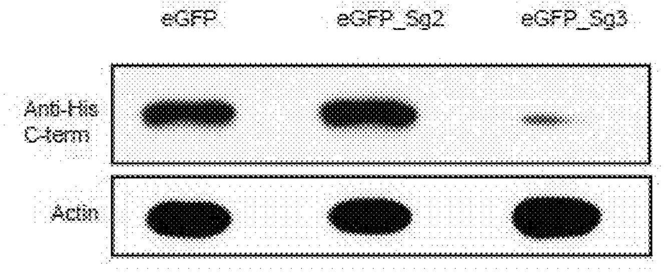

An original approach to study this mechanism was used. This was done by splitting the mRNA sequence into three fragments and comparing the expression of these fragments with and without an inhibitor of protein degradation (FIG. 1B). With this approach it was shown that the translation C-term terminal fragment (Seg3) was repressed (FIG. 1C) indicating the presence of a novel translational control mechanism in this region that regulates the translation of the whole transcript. This was confirmed by experiments that showed Seg3 prevented the translation of the central segment (Seg2) that was capable of high level of translation (FIG. 1D). It was also shown that the regulatory mechanism for the translation of the Seg3 was present in the mRNA (FIG. 1E). Additional support was provided by the experiments which showed the fusion a reporter gene (eGFP) with the Seg3 and inserting two stop codons in between the two sequences repressed the translation of eGFP (FIG. 2).

Figure 3A:
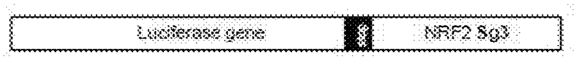
FIGS. 3A to 3D show the construction of a translation reporter system to identify compounds that derepress Nrf2 translation.
Figure 3B:
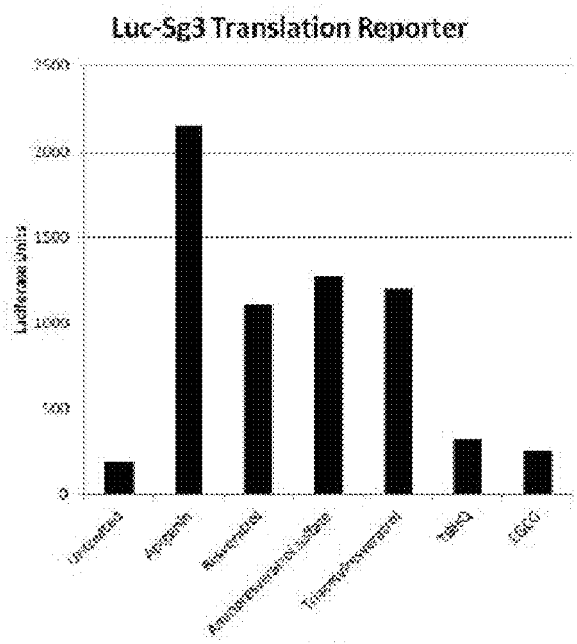
Figure 3C:
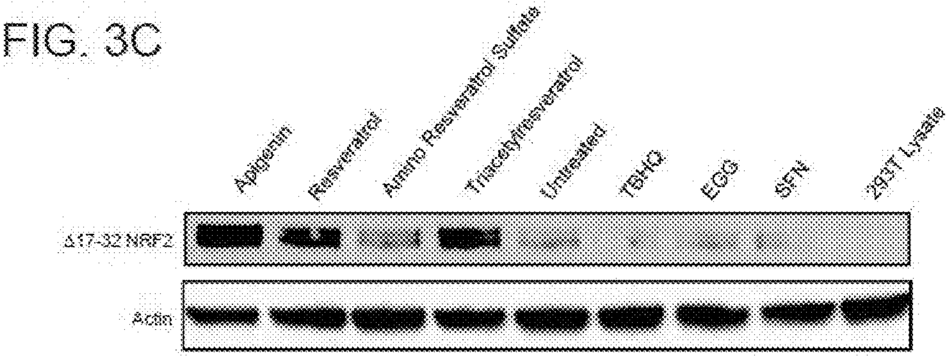
Figure 3D:
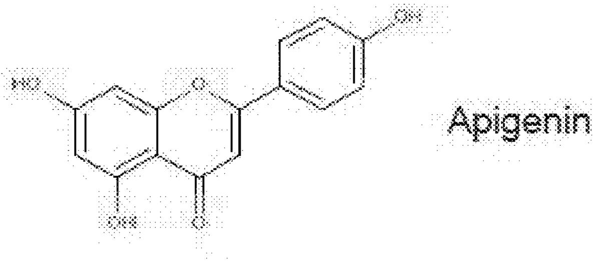
Figure 3D:
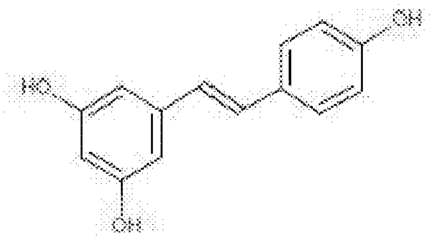
Figure 3D:
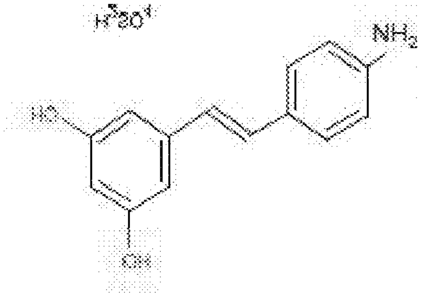
Figure 3D:
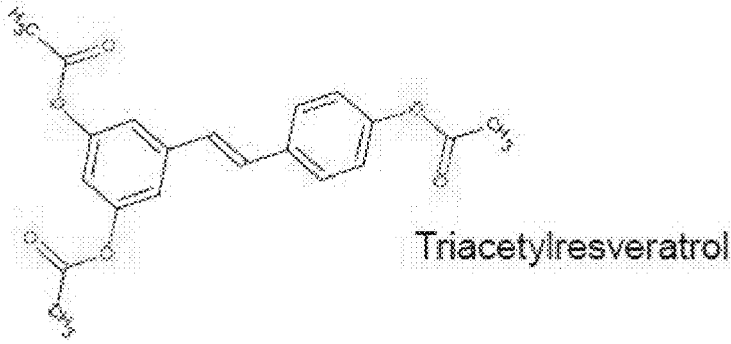

Based on these findings, a novel Nrf2 translation biosensor was created that allows a high throughput screening of compounds which are able to directly promote Nrf2 translation (FIG. 3A). A construct containing the luciferase gene fused with the Seg3 with stop codons in between the two fragments was developed. A library of 127 well known antioxidants was screened. Apigenin, resveratrol and 2 analogs of resveratrol promoted the translation of Nrf2 (FIGS. 3B and 3C). Although these compounds have been previously been shown to promote an antioxidant response, their ability to promote Nrf2 translation is a novel finding.

Apigenin was identified as a potent activator of NRF2 translation. Apigenin can be used as a positive control molecule to identify novel modulators of NRF2 translation. NRF2 translation inhibitors can be found by exposing the biosensor to molecules in chemical libraries, followed by treatment with apigenin, novel nrf2 translation inhibitors will prevent the activation of translation promoted by apigenin, these experiments can be done in vivo or in vitro systems.

Figure 4:
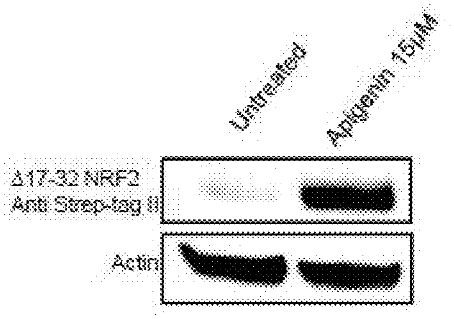
FIG. 4 are blots showing the ability of apigenin analogs to directly activate the translation of Nrf2. Since apigenin was the most potent inducer of Nrf2 translation, the ability of two other analogs of apigenin to de-repress Nrf2 translation was evaluated. Both quercetin and luteolin with similar structure to apigenin increase the translation of Nrf2.
Figure 4:
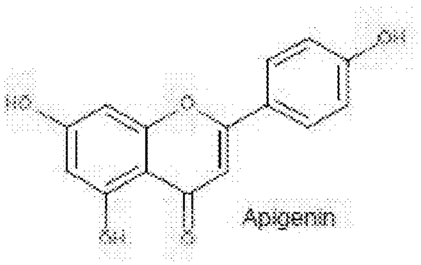
Figure 4:
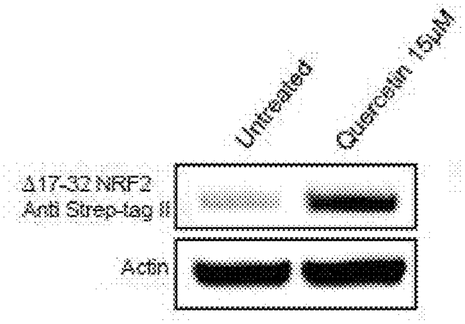
Figure 4:
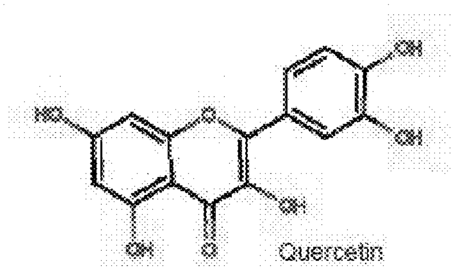
Figure 4:
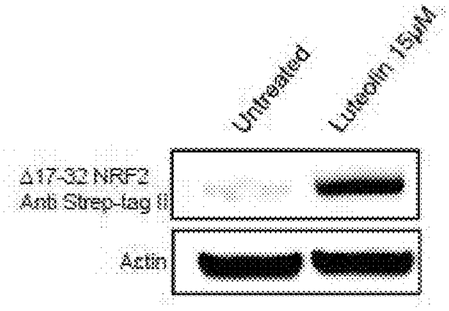
Figure 4:
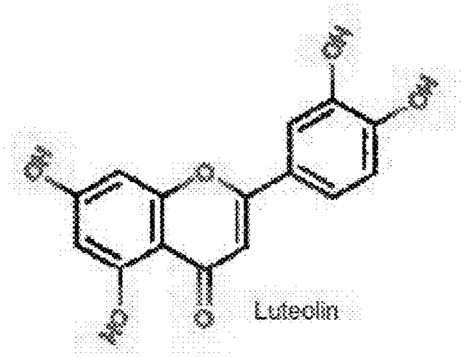
Figure 5:
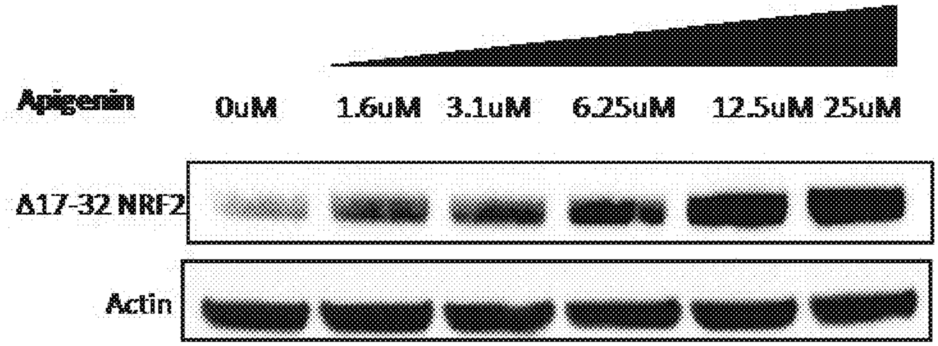
FIG. 5 is a blot showing that Apigenin activates Nrf2 translation in a dose-dependent manner. HEK293T cells were transfected with an Nrf2 construct lacking amino acids that are required for KEAP1 mediated degradation. 24 hours later the cells were treated with Apigenin in incremental doses to evaluate Nrf2 translation activation by using Western blotting.
Figure 6:
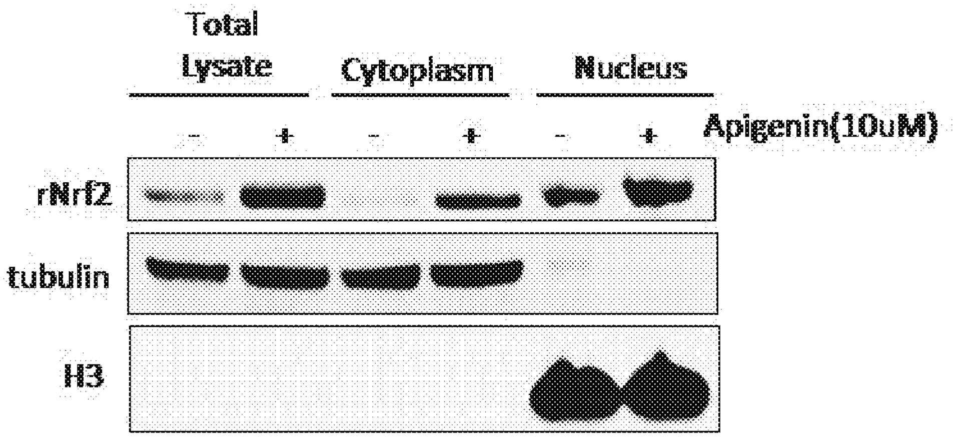
FIG. 6 is a blot showing the nuclear translocation of Nrf2 after translation activation by Apigenin. HEK293T cells were transfected with a plasmid containing the wildtype sequence of Nrf2. After 24 hours the cells were treated with Apigenin. After additional 12 hours, the cells were harvested and subjected to subcellular fractionation. The presence of Nrf2 in the cytoplasm and nucleus was evaluated using Western blotting. Additionally, tubulin and histone 3 were identified by Western blot to validate the subcellular fractionation.

Collectively these data indicate that an Nrf2 translation biosensor can be used as a tool to discover novel potent inducers of Nrf2. It was also shown that compounds with a similar chemical structure to the apigenin are able to promote the translation of Nrf2 providing evidence that a family of compounds that potently activates NRF2 translation can be found (FIG. 4).

Figure 7A:
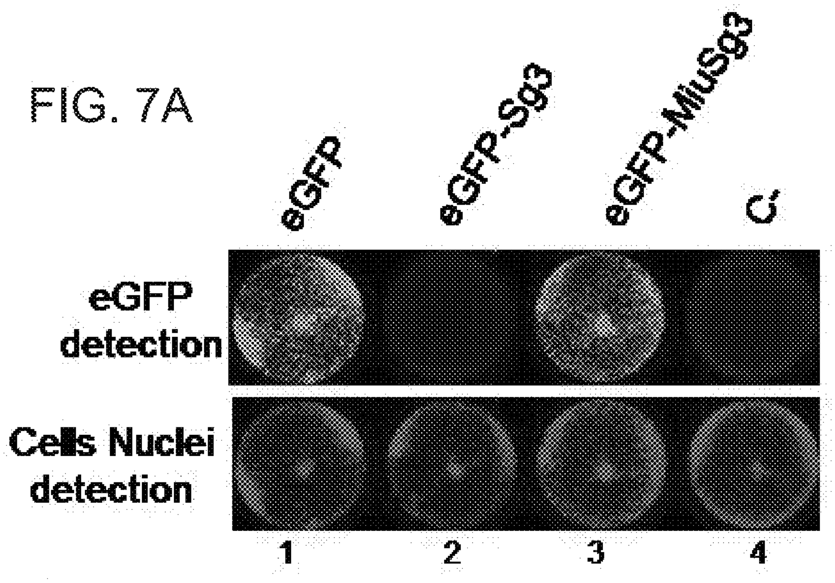
FIGS. 7A and 7B show synonym mutations of Segment 3 reverse translational repression.
Figure 7B:
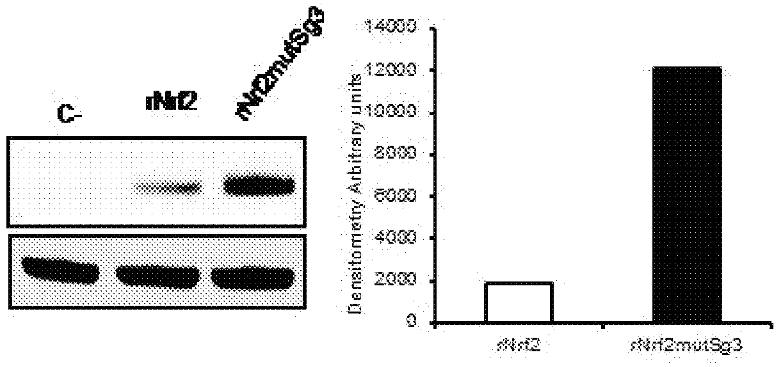

The minimum sequence required in the Seg3 to maintain translational control was identified. This discovery can be also applicable to overexpress Nrf2 in cell culture or in gene therapy applications by mutating or deleting this region. Any synonym codon substitution of segment 3 reverses the translational repression mechanism for Nrf2 (FIGS. 7A, 7B)

Sequence of Nrf2 and Sg3.

The mRNA sequence of NRF-2 corresponding to NCBI Reference Sequence: NM_006164.4 was used to extract the open reading frame (ORF) of NRF2. Sg3 is contained between nucleotides 1159-1818 in the ORF of NRF2 and is shown by the shaded area.

Nrf2 (SEQ ID NO: 1):

ATGATGGACTTGGAGCTGCCGCCGCCGGGACTCCCGTCCCAGCAGGACA
TGGATTTGATTGACATACTTTGGAGGCAAGATATAGATCTTGGAGTAAG
TCGAGAAGTATTTGACTTCAGTCAGCGACGGAAAGAGTATGAGCTGGAA
AAACAGAAAAAACTTGAAAAGGAAAGACAAGAACAACTCCAAAAGGAGC
AAGAGAAAGCCTTTTTCGCTCAGTTACAACTAGATGAAGAGACAGGTGA
ATTTCTCCCAATTCAGCCAGCCCAGCACATCCAGTCAGAAACCAGTGGA
TCTGCCAACTACTCCCAGGTTGCCCACATTCCCAAATCAGATGCTTTGT
ACTTTGATGACTGCATGCAGCTTTTGGCGCAGACATTCCCGTTTGTAGA
TGACAATGAGGTTTCTTCGGCTACGTTTCAGTCACTTGTTCCTGATATT
CCCGGTCACATCGAGAGCCCAGTCTTCATTGCTACTAATCAGGCTCAGT
CACCTGAAACTTCTGTTGCTCAGGTAGCCCCTGTTGATTTAGACGGTAT
AGCACAGGACATTGAGCAAGTTTGGGAGGAGCTATTATCCATTCCTGAG
TTACAGTGTCTTAATATTGAAAATGACAAGCTGGTTGAGACTACCATGG
TTCCAAGTCCAGAAGCCAAACTGACAGAAGTTGACAATTATCATTTTTA
CTCATCTATACCCTCAATGGAAAAAGAAGTAGGTAACTGTAGTCCACAT
TTTCTTAATGCTTTTGAGGATTCCTTCAGCAGCATCCTCTCCACAGAAG
ACCCCAACCAGTTGACAGTGAACTCATTAAATTCAGATGCCACAGTCAA
CACAGATTTTGGTGATGAATTTTATTCTGCTTTCATAGCTGAGCCCAGT
ATCAGCAACAGCATGCCCTCACCTGCTACTTTAAGCCATTCACTCTCTG
AACTTCTAAATGGGCCCATTGATGTTTCTGATCTATCACTTTGCAAAGC
TTTCAACCAAAACCACCCTGAAAGCACAGCAGAATTCAATGATTCTGAC
TCCGGCATTTCACTAAACACAAGTCCCAGTGTGGCATCACCAGAACACT
CAGTGGAATCTTCCAGCTATGGAGACACACTACTTGGCCTCAGTGATTC
TGAAGTGGAAGAGCTAGATAGTGCCCCTGGA
AGTGTCAAACAGAATGGTCCTAAAACACCAGTACATTCTTCTGG
GGATATGGTACAACCCTTGTCACCATCTCAGGGGCAGAGCACTCACGTGC
ATGATGCCCAATGTGAGAACACACCAGAGAAAGAATTGCCTGTAAGTCCT
GGTCATCGGAAAACCCCATTCACAAAAGACAAACATTCAAGCCGCTTGGA
GGCTCATCTCACAAGAGATGAACTTAGGGCAAAAGCTCTCCATATCCCAT
TCCCTGTAGAAAAAATCATTAACCTCCCTGTTGTTGACTTCAACGAAATG
ATGTCCAAAGAGCAGTTCAATGAAGCTCAACTTGCATTAATTCGGGATAT
ACGTAGGAGGGGTAAGAATAAAGTGGCTGCTCAGAATTGCAGAAAAAGAA
AACTGGAAAATATAGTAGAACTAGAGCAAGATTTAGATCATTTGAAAGAT
GAAAAAGAAAAATTGCTCAAAGAAAAAGGAGAAAATGACAAAAGCCTTC
ACCTACTGAAAAAACAACTCAGCACCTTATATCTCGAAGTTTTCAGCATG
CTACGTGATGAAGATGGAAAACCTTATTCTCCTAGTGAATACTCCCTGCA
GCAAACAAGAGATGGCAATGTTTTCCTTGTTCCCAAAAGTAAGAAGCCAG
ATGTTAAGAAAAACTAG

Sg3 is compose by nucleotides 1159-1818 in the ORF of NRF2.

Sg3 (SEQ ID NO: 2):

```
AGTGTCAAACAGAATGGTCCTAAAACACCAGTACATTCTTCTGGGGAT
ATGGTACAACCCTTGTCACCATCTCAGGGGCAGAGCACTCACGTGCAT
GATGCCCAATGTGAGAACACACCAGAGAAAGAATTGCCTGTAAGTCCT
GGTCATCGGAAAACCCCATTCACAAAAGACAAACATTCAAGCCGCTTG
GAGGCTCATCTCACAAGAGATGAACTTAGGGCAAAAGCTCTCCATATC
CCATTCCCTGTAGAAAAAATCATTAACCTCCCTGTTGTTGACTTCAAC
GAAATGATGTCCAAAGAGCAGTTCAATGAAGCTCAACTTGCATTAATT
CGGGATATACGTAGGAGGGGTAAGAATAAAGTGGCTGCTCAGAATTGC
AGAAAAAGAAAACTGGAAAATATAGTAGAACTAGAGCAAGATTTAGAT
CATTTGAAAGATGAAAAAGAAAAATTGCTCAAAGAAAAAGGAGAAAAT
GACAAAAGCCTTCACCTACTGAAAAAACAACTCAGCACCTTATATCTC
GAAGTTTTCAGCATGCTACGTGATGAAGATGGAAAACCTTAGTGAAAT
TCTCCTTACTCCCTGCAGCAAACAAGAGATGGCAATGTTTTCCTTGTT
CCCAAAAGTAAGAAGCCAGATGTTAAGAAAAACTAG.
```

Sequence of Luc2-stop-Sg3 (SEQ ID NO: 3):

A stop codon is indicated with bold letters and a dark grey shade. The sequence corresponding to sg3 is indicated in the light grey shade area. The sequence was expressed using a plasmid with a CMV promoter.

Luc2-stop-Sg3 (SEQ ID NO: 3):

ATGGAAGATGCCAAAAACATTAAGAAGGGCCCAGCGCCATTCTACCCACT
CGAAGACGGGACCGCCGGCGAGCAGCTGCACAAAGCCATGAAGCGCTACG
CCCTGGTGCCCGGCACCATCGCCTTTACCGACGCACATATCGAGGTGGAC
ATTACCTACGCCGAGTACTTCGAGATGAGCGTTCGGCTGGCAGAAGCTAT
GAAGCGCTATGGGCTGAATACAAACCATCGGATCGTGGTGTGCAGCGAGA
ATAGCTTGCAGTTCTTCATGCCCGTGTTGGGTGCCCTGTTCATCGGTGTG
GCTGTGGCCCCAGCTAACGACATCTACAACGAGCGCGAGCTGCTGAACAG
CATGGGCATCAGCCAGCCCACCGTCGTATTCGTGAGCAAGAAAGGGCTGC
AAAAGATCCTCAACGTGCAAAAGAAGCTACCGATCATACAAAAGATCATC
ATCATGGATAGCAAGACCGACTACCAGGGCTTCCAAAGCATGTACACCTT
CGTGACTTCCCATTTGCCACCCGGCTTCAACGAGTACGACTTCGTGCCCG
AGAGCTTCGACCGGGACAAAACCATCGCCCTGATCATGAACAGTAGTGGC
AGTACCGGATTGCCCAAGGGCGTAGCCCTACCGCACCGCACCGCTTGTGT
CCGATTCAGTCATGCCCGCGACCCCATCTTCGGCAACCAGATCATCCCCG
ACACCGCTATCCTCAGCGTGGTGCCATTTCACCACGGCTTCGGCATGTTC
ACCACGCTGGGCTACTTGATCTGCGGCTTTCGGGTCGTGCTCATGTACCG
CTTCGAGGAGGAGCTATTCTTGCGCAGCTTGCAAGACTATAAGATTCAAT

-continued

CTGCCCTGCTGGTGCCCACACTATTTAGCTTCTTCGCTAAGAGCACTCTC
ATCGACAAGTACGACCTAAGCAACTTGCACGAGATCGCCAGCGGCGGGGC
GCCGCTCAGCAAGGAGGTAGGTGAGGCCGTGGCCAAACGCTTCCACCTAC
CAGGCATCCGCCAGGGCTACGGCCTGACAGAAACAACCAGCGCCATTCTG
ATCACCCCCGAAGGGGACGACAAGCCTGGCGCAGTAGGCAAGGTGGTGCC
CTTCTTCGAGGCTAAGGTGGTGGACTTGGACACCGGTAAGACACTGGGTG
TGAACCAGCGCGGCGAGCTGTGCGTCCGTGGCCCCATGATCATGAGCGGC
TACGTTAACAACCCCGAGGCTACAAACGCTCTCATCGACAAGGACGGCTG
GCTGCACAGCGGCGACATCGCCTACTGGGACGAGGACGAGCACTTCTTCA
TCGTGGACCGGCTGAAGAGCCTGATCAAATACAAGGGCTACCAGGTAGCC
CCAGCCGAACTGGAGAGCATCCTGCTGCAACACCCCAACATCTTCGACGC
CGGGGTCGCCGGCCTGCCCGACGACGATGCCGGCGAGCTGCCCGCCGCAG
TCGTCGTGCTGGAACACGGTAAAACCATGACCGAGAAGGAGATCGTGGAC
TATGTGGCCAGCCAGGTTACAACCGCCAAGAAGCTGCGCGGTGGTGTTGT
GTTCGTGGACGAGGTGCCTAAAGGACTGACCGGCAAGTTGGACGCCCGCA
AGATCCGCGAGATTCTCATTAAGGCCAAGAAGGGCGGCAAGATCGCCGTG
TAAAGTGTCAAACAGAATGGTCCTAAAACACCAGTACATTCTTCTGGGGA
TATGGTACAACCCTTGTCACCATCTCAGGGGCAGAGCACTCACGTGCATG
ATGCCCAATGTGAGAACACACCAGAGAAAGAATTGCCTGTAAGTCCTGGT
CATCGGAAAACCCCATTCACAAAAGACAAACATTCAAGCCGCTTGGAGGC
TCATCTCACAAGAGATGAACTTAGGGCAAAAGCTCTCCATATCCCATTCC
CTGTAGAAAAAATCATTAACCTCCCTGTTGTTGACTTCAACGAAATGATG
TCCAAAGAGCAGTTCAATGAAGCTCAACTTGCATTAATTCGGGATATACG
TAGGAGGGGTAAGAATAAAGTGGCTGCTCAGAATTGCAGAAAAAGAAAACT
GGAAAATATAGTAGAACTAGAGCAAGATTTAGATCATTTGAAAGATGAAA
AAGAAAAATTGCTCAAAGAAAAAGGAGAAAATGAACAAAAGCCTTCACCTA
CTGAAAAAACAACTCAGCACCTTATATCTCGAAGTTTTCAGCATGCTACG
TGATGAAGATGGAAAACCTTATTCTCCTAGTGAATACTCCCTGCAGCAAA
CAAGAGATGGCAATGTTTTCCTTGTTCCCAAAAGTAAGAAGCCAGATGTT
AAGAAAAACTAG.

Indicates the location of segment 3 and highlights the exact sequence of this portion. The data shows that the modification of the codons in this particular segment with synonymous mutation, abolished the translational repression of Nrf2. This novel sequence does not exist in nature and is applicable for utility for gene therapy or administration of the molecule, encoded or otherwise, to a patient in need of such therapy.

The sequence of the modified Segment 3 is:

(SEQ ID NO: 4)

TCGGTTAAGCAAAACGGCCCAAAGACGCCCGTCCACTCGTCAGGTGACAT
GGTCCAGCCACTGTCCCCCTCGCAAGGACAAAGTACGCATGTACACGACG

CTCAGTGCGAAAATACCCCCGAAAAGGAGCTACCCGTGTCCCCCGGGCAC

AGAAAGACGCCCTTTACGAAGGATAAGCACTCCTCCAGGTTAGAAGCCCA

CCTAACGCGCGACGAGCTCCGAGCGAAGGCGTTACACATACCCTTTCCCG

TGGAGAAGATAATAAATTTGCCGGTAGTCGATTTTAATGAGATGATGAGT

AAGGAACAATTTAACGAGGCCCAGCTAGCGTTGATAAGGGACATCAGACG

CCGAGGAAAAAACAAGGTAGCAGCGCAAAACTGTCGGAAGCGGAAGTTAG

AGAACATCGTGGAGCTCGAACAGGACCTCGACCACCTAAAGGACGAGAAG

GAGAAGCTCCTAAAGGAGAAGGGGGAGAACGATAAGTCATTGCATTTGCT

AAAGAAGCAGTTGTCGACTTTGTACTTAGAGGTATTTTCTATGTTGCGGG

ACGAGGACGGCAAGCCCTACTCGCCCTCAGAGTATTCGCTCCAACAGACC

CGAGACGGTAACGTCTTTCTAGTCCCTAAGTCCAAAAAACCCGACGTGAA

AAAGAAT.

The modified Segment 3 (SEQ ID NO: 4) may comprise any other synonym codon mutation combination and these would also increase translation of Nrf2.

The Abstract of the disclosure will allow the reader to quickly ascertain the nature of the technical disclosure. It is submitted with the understanding that it will not be used to interpret or limit the scope or meaning of the following claims.

What is claimed:

1. A method of screening for an agent that modulates the translation of Nuclear factor-erythroid 2 related factor 2 (Nrf2), the method comprising:

a) providing a mammalian cell expressing a biosensor, wherein the biosensor comprises a nucleic acid encoding a reporter gene having a 5' end and a 3' end, wherein the nucleic acid encoding the reporter gene is fused at the 3' end to a linker nucleic acid comprising at least one stop codon and having a 5' end and a 3' end, and wherein the linker is fused at the 3' end to a nucleic acid encoding a C-terminal fragment of Nuclear factor-erythroid 2 related factor 2 (Nrf2) and wherein the nucleic acid encoding the C-terminal fragment of Nuclear factor-erythroid 2 related factor 2 (Nrf2) is SEQ ID NO: 2;

b) contacting the mammalian cell with an agent;

c) measuring the expression of the reporter gene; and d) comparing the measured level of expression of the reporter gene to a measured level of expression in a control mammalian cell comprising the biosensor in the absence of the agent, wherein an increase in reporter gene expression in the presence of the agent indicates that the agent modulates the translation of Nuclear factor-erythroid 2 related factor 2 (Nrf2).

2. The method of claim 1, wherein the reporter gene encodes luciferase, green fluorescent protein, red fluorescent protein, yellow fluorescent protein, cyan fluorescent protein, alkaline phosphatase, beta galactosidase, beta glucuronidase, chloramphenicol acetyltransferase, horseradish peroxidase, acetohydroxyacid synthase, nopaline synthase, or octopine synthase.

3. The method of claim 1, wherein the reporter gene encodes a luciferase.

4. The method of claim 1, wherein the reporter gene encodes a green fluorescent protein.

5. The method of claim 1, wherein the measuring step comprises a luminescence assay, a chemiluminescence assay, a fluorescence assay or an enzymatic assay.

6. A method of screening for an agent that modulates the translation of Nuclear factor-erythroid 2 related factor 2 (Nrf2), the method comprising:

a) providing a mammalian cell expressing a biosensor according to SEQ ID NO: 3, which comprises a nucleic acid sequence encoding a luciferase gene, a linker nucleic acid comprising a stop codon, and a nucleic acid sequence encoding a C-terminal fragment of Nuclear factor-erythroid 2 related factor 2 (Nrf2);

b) contacting the mammalian cell with an agent;

c) measuring the expression of luciferase; and d) comparing the measured level of expression of luciferase to a measured level of expression in a control mammalian cell comprising the biosensor in the absence of the agent, wherein an increase in luciferase expression in the presence of the agent indicates that the agent modulates the translation of Nuclear factor-erythroid 2 related factor 2 (Nrf2).

* * * * *